United States Patent
Kiefer et al.

(10) Patent No.: US 7,841,989 B2
(45) Date of Patent: Nov. 30, 2010

(54) ELECTROMAGNETIC PERSONNEL INTERDICTION CONTROL METHOD AND SYSTEM

(75) Inventors: Karl F. Kiefer, Conroe, TX (US); Kevin Champaigne, Conroe, TX (US); Gulnara Ajupova, Conroe, TX (US)

(73) Assignee: Invocon, Inc., Conroe, TX (US)

( * ) Notice: Subject to any disclaimer, the term of this patent is extended or adjusted under 35 U.S.C. 154(b) by 1323 days.

(21) Appl. No.: 11/243,687

(22) Filed: Oct. 4, 2005

(65) Prior Publication Data

US 2007/0249959 A1   Oct. 25, 2007

Related U.S. Application Data (60) Provisional application No. 60/615,703, filed on Oct. 4, 2004.

(51) Int. Cl.
*A61B 5/00* (2006.01)
*A61B 5/103* (2006.01)
*A61B 5/117* (2006.01)
*F42B 8/00* (2006.01)
*F42B 10/00* (2006.01)
*F42B 12/00* (2006.01)
*F42B 14/06* (2006.01)
*F42B 30/00* (2006.01)
*F41C 9/00* (2006.01)
*H04B 1/02* (2006.01)

(52) U.S. Cl. .............. 600/559; 600/552; 600/587; 102/502; 42/1.08; 367/139

(58) Field of Classification Search .............. 600/300, 600/372, 382, 383, 407, 437, 439, 544, 546, 600/547, 552, 554, 558, 559, 587, 595; 606/1, 606/32, 33, 34, 41, 42; 607/1, 2, 3, 45, 48, 607/53, 54, 55, 56, 154; 342/22; 367/137, 367/139, 199; 361/230, 232; 89/1.11; 42/1.08; 102/501, 502
See application file for complete search history.

(56) References Cited

U.S. PATENT DOCUMENTS 4,611,599 A * 9/1986 Bentall et al. .............. 607/27

(Continued)

OTHER PUBLICATIONS

Miller, Diane F., "Basics of Radio Astronomy" Mar. 1997, California Institute of Technology, JPL D-13835.*

(Continued)

*Primary Examiner*—Max Hindenburg
*Assistant Examiner*—Jeffrey G Hoekstra
(74) *Attorney, Agent, or Firm*—Kenneth A. Roddy (57) ABSTRACT

A non-lethal and non-destructive electromagnetic personnel interdiction control stun type weapon system and method utilizes beamed radio frequency energy in a frequency range and modulated to impose a Lorentz force on the vestibular system or sensory cells of a remote human subject sufficient to disrupt the mechanical transduction process and/or the chemical engine by which sound, position and other sensory input are converted to messages by nerve cells and processed by the brain to produce complete disorientation, confusion, and incapacitation sufficient to temporarily render the subject powerless to resist arrest or subjugation. Removal of the electromagnetic energy leaves the nerve cells and surrounding tissues with no damage and second order effects of severe motion sickness and psychological effects of helplessness remains until the subject's body chemistry returns to normal.

6 Claims, 6 Drawing Sheets

U.S. PATENT DOCUMENTS

| | | | |
|---|---|---|---|
| 5,787,340 A | | 7/1998 | Sepponen |
| 5,935,054 A | * | 8/1999 | Loos .............................. 600/9 |
| 6,077,237 A | * | 6/2000 | Campbell et al. ........... 600/587 |
| 6,238,333 B1 | | 5/2001 | Loos |
| 6,314,324 B1 | | 11/2001 | Lattner et al. |
| 7,277,749 B2 | * | 10/2007 | Gordon et al. ................. 607/2 |
| 2002/0072781 A1 | * | 6/2002 | Lattner et al. ................. 607/42 |

OTHER PUBLICATIONS

Bozovic D, Hudspeth, A. J., "Hair-bundle movements elicited by transepithelial electrical stimulation of hair cells in the sacculus of the bullfrog", Proc Natl Acad Sci U S A.

* cited by examiner

Fig. 8 Modulation scheme for EPIC signal. Upper panel shows a signal with two consequent pulses. Lower panel is a zoom into the first half-wave of the pulse.

*Fig. 9* Magnetic field strength required to create 15 nm displacement. Field is plotted as a function of driving frequency at various values of resting current.

ELECTROMAGNETIC PERSONNEL INTERDICTION CONTROL METHOD AND SYSTEM

CROSS REFERENCE TO RELATED APPLICATION

This application claims priority of U.S. Provisional Application Ser. No. 60/615,703, filed Oct. 4, 2004.

STATEMENT REGARDING FEDERALLY SPONSORED RESEARCH

This invention was made with Government support under DOD Small Business Innovation Research (SBIR) Contract No. M67854-04-C-1013 awarded by the U.S. Marine Corps Systems Command.

BACKGROUND OF THE INVENTION

1. Field Of The Invention

This invention relates generally to non-destructive stun weapons, and, more particularly to a non-destructive stun type weapon that utilizes beamed electromagnetic RF energy (Lorentz Force) that disrupts the normal mechanical transduction process and/or the chemical engine by which sound, position and other sensory input are converted to messages by nerve cells and processed by the brain to produce complete disorientation and confusion to temporarily and remotely render a human powerless to resist arrest or subjugation.

2. Background Art

There is a long-felt need in the military and in law enforcement for a non-destructive stun type weapon that would remotely incapacitate a hostile war fighter, terrorist, or criminal suspect ineffective for a period of time without permanent damage.

The US military has achieved improved accuracy and the ability to target small objectives with precision that precludes widespread collateral damage. These improvements are in air-to-ground munitions as well as ground-to-ground weapons. This precise destruction of "hostile military targets" while allowing adjacent personnel and structures to survive with no damage has broadened the ability of political decision makers to respond with "measured response" force to threats of terror and hostile military actions. These responses are more politically acceptable since innocent civil casualties are kept at a minimum. The desirability of waging bloodless war to counter threats to national security is virtually limitless since both military and civil authority could determine a priori when and if loss of human life is necessary.

Clinical evidence demonstrates that hearing and equilibrium disruption may result from disease and side effects from medication. Considerable efforts are being made to better understand the mechanics of the inner ear so that effective treatments may be made available to counter the debilitating effects of mechanical and chemical disruption of normal human functions. However, the existence of these debilitating effects prove that chemical interruption of inner ear processes can produce effects that are desirable for a stun type weapon if they are not permanent.

The human vestibular system is remarkably sturdy under a variety of conditions. Yet, it has been proven vulnerable. Most of the time, the vestibular loss is transient. However, in some cases the loss is recurring, escalating and, ultimately, permanent. There are several levels at which the vestibular function can be affected: interference with the function of the central nervous system components of balance and the interruption of the hair cell's transduction process. The means to interfere with the nervous system would be to emulate, for example, the stimuli of the motion sickness, which can be quite debilitating. Visual stimulations such as virtual reality or virtual simulator sickness are also classed as disruption at the level of the central nervous system.

Various chemicals and drugs are known that disrupt the function of vestibular hair cells themselves. Calcium channel blockers interfere with normal function at the hair bundle level. Other drugs disrupt the synaptic and post-synaptic process. Yet other drugs cause death of the hair cell itself. The vestibulotoxic medications are also used to suppress vestibular function to treat vestibular disorders, such as vertigo and vestibular migraine. However, inducing chemical changes in the body without contact is not an easy path.

The normal operation of the cells of the ear, vestibular system, and the eye can also be disrupted by increasing or decreasing the magnitude of the static charge on the particular cell membranes to adversely affect its attraction to calcium (Ca) and/or potassium (K) ions and thereby impact the rate of ion flow and the ultimate pulse rate of the cells. Uncorrelated data would then be fed to the brain and the brain would have no basis for decoding, thereby creating disorientation.

Altering the normal electromagnetic field and subsequent surfaces charges on the tissues of the ear, vestibular system and the eye can change the impedance of their conduction capabilities, disturb the ion flow, and subsequently impact the pulse output of the cells to the brain. This interruption of normal ion flow would cause pulse patterns to the brain that it cannot decode, thereby creating disorientation.

The normal electrochemical balance of substantially all of the cells of the human body relative to the rest of the body fluids can be disrupted by altering the relative charge level to cause the cells to activate the protein doors or cation channels in the cell wall that allow unidirectional passage of negative charge sodium (Na) ions and the opposite passage of positively charged calcium (Ca) ions, thereby causing hyperactive chemical exchanges that can negatively impact the system and disrupt normal smooth and striated muscular functions.

The application of pulses of voltage directly to nerve paths can also feed uncorrelated sensory input data to the brain that would ultimately produce some level of disorientation.

It is well known in the field of physics that electromagnetic radio frequency energy can actually excite physical movement in devices that are tuned to sympathetic resonance, and certain resonant structures can respond to and demodulate high frequency radio carrier energy.

The present invention is distinguished over the prior art in general by an electromagnetic personnel interdiction control (EPIC) non-destructive stun type weapon and method that utilizes beamed electromagnetic RF energy (Lorentz Force) to excite and interrupt the normal process of human hearing, equilibrium and other senses to produce complete disorientation and confusion. This is accomplished by: (1) interruption of the mechanical transduction process by which sound, position (relative to gravity) and other sensory input is converted to messages that are processed by the brain; and (2) interruption of the chemical engine which sustains the proper operation of nerve cells that respond to the mechanical transduction mechanisms. Interruption of either or both of these processes produces complete disorientation and confusion sufficient to temporarily and remotely render a human powerless to resist arrest or subjugation.

The present invention provides a minimum destruction weapon that can temporarily incapacitate a human threat as a point or area target and will operate through walls and other protective mediums that now provide cover for combatants in urban warfare situations. It provides an individual soldier or law enforcement officer with the ability to reduce an opponent to helplessness from a remote location while doing no permanent damage. Such a weapon has significant utility for use by military units in an assault situation, allowing them to remotely subdue and capture hostile war fighters, terrorists, and large numbers of prisoners that would result from the "stun and restrain" tactic. The damage of friendly fire mistakes would be minimized since no permanent damage would be done by the stun weapon. Used in "special operations" raid scenarios, the prisoner issues would not be critical since the raid would be in and out before the complete recovery of stunned combatants. It also has significant utility for use by law enforcement personnel, allowing them to remotely incapacitate criminal suspects or rioters from a remote location and render them ineffective for a period of time without permanent damage.

SUMMARY OF THE INVENTION

It is therefore an object of the present invention to provide an electromagnetic personnel interdiction control (EPIC) non-destructive stun type weapon apparatus and method that utilizes beamed RF energy (Lorentz Force) to remotely excite the human vestibular inner ear system and interrupt the normal process of human hearing and equilibrium and thereby produce complete disorientation, confusion, and temporary incapacitation sufficient to render a human powerless to resist arrest or subjugation.

It is another object of this invention to provide an electromagnetic personnel interdiction control (EPIC) non-destructive stun type weapon apparatus and method that utilizes electromagnetic waves to interfere with vestibular function by applying Lorentz Force on the ionic currents in the cilia of the human inner ear to cause extraneous motion of the entire ciliary bundle thereby creating disorienting input to the brain resulting in a reaction that produces complete disorientation and confusion and will render a person inoperable for the duration of the stimulus and for a short time thereafter.

Another object of this invention is to provide an electromagnetic personnel interdiction control (EPIC) non-destructive stun type weapon apparatus and method that produces complete disorientation and confusion utilizing electromagnetic waves to interfere with vestibular function by transmitting radio frequency transmissions having a frequency and modulation correlated to the physical and chemical structure of the human inner ear transduction process to: (1) interrupt the mechanical transduction process by which sound and position (relative to gravity) are converted to messages that are processed by the brain; and (2) interrupt the chemical engine which sustains the proper operation of the nerve cells that respond to the mechanical transduction mechanisms.

Another object of this invention is to provide a non-destructive stun type weapon for use by military and law enforcement personnel that will remotely incapacitate a hostile war fighter, terrorist, or criminal suspect from a remote location and render them ineffective for a period of time without permanent damage.

Another object of this invention is to provide a non-destructive stun type weapon for use by military and law enforcement personnel that provides a weapon that can temporarily incapacitate a human threat as a point or area target.

Another object of this invention is to provide a non-destructive stun type weapon for military personnel for use in an assault situation, allowing military units to remotely subdue, and capture, large numbers of prisoners that would result from the "stun and restrain" tactic, without shooting or gunfire.

Another object of this invention is to provide a non-destructive stun type weapon for use by military and law enforcement personnel that can operate through walls and other protective mediums that now provide cover for combatants to temporarily incapacitate the combatant threat.

Another object of this invention is to provide a non-destructive stun type weapon for use by military and law enforcement personnel that will disrupt the normal operation of the cells of the ear, vestibular system, and the eye by increasing or decreasing the magnitude of the static charge on the particular cell membranes to adversely affect its attraction to calcium (Ca) and/or potassium (K) ions and thereby impact the rate of ion flow and the ultimate pulse rate of the cells, such that uncorrelated data would then be fed to the brain and the brain would have no basis for decoding, thereby creating disorientation.

Another object of this invention is to provide a non-destructive stun type weapon for use by military and law enforcement personnel that will alter the normal electromagnetic field and subsequent surfaces charges on the tissues of the ear, vestibular system and the eye and change the impedance of their conduction capabilities, disturb the ion flow, and subsequently impact the pulse output of the cells to the brain to produce pulse patterns that it cannot decode, thereby creating disorientation.

Another object of this invention is to provide a non-destructive stun type weapon for use by military and law enforcement personnel that is capable of disrupting the normal electrochemical balance of various cells of the human body relative to the rest of the body fluids by altering the relative charge level to cause the cells to activate the protein doors or cation channels in the cell wall that allow unidirectional passage of negative charge sodium (Na) ions and the opposite passage of positively charged calcium (Ca) ions, thereby causing hyperactive chemical exchanges that can negatively impact the system and disrupt normal smooth and striated muscular functions.

Another object of this invention is to provide a non-destructive stun type weapon for use by military and law enforcement personnel that is capable of remotely applying pulses of voltage directly to nerve paths to feed uncorrelated sensory input data to the brain that would produce disorientation.

A further object of this invention is to provide an electromagnetic personnel interdiction control (EPIC) apparatus and method for use in medical applications to correct or alleviate symptoms of dizziness, Benign Paroxysmal Positional Vertigo (BPPV), disorientation, lightheadedness, imbalance, nausea, and confusion, utilizing electromagnetic waves to enhance vestibular function by transmitting radio frequency transmissions having a frequency and modulation correlated to the physical and chemical structure of the human inner ear transduction process to: (1) normalize the mechanical transduction process by which sound and position (relative to gravity) are converted to messages that are processed by the brain; and/or (2) normalize the chemical engine which sustains the proper operation of the nerve cells that respond to the mechanical transduction mechanisms.

A still further object of this invention is to provide a non-destructive stun type weapon for use by military and law enforcement personnel that will remotely incapacitate a hostile human combatant that is inexpensive to manufacture, quick and easy to implement, and safe and reliable in operation.

Other objects of the invention will become apparent from time to time throughout the specification and claims as hereinafter related.

The above noted objects and other objects of the invention are accomplished by an electromagnetic personnel interdiction control (EPIC) non-destructive stun type weapon apparatus and method that utilizes beamed RF energy (Lorentz Force) to excite and interrupt the normal process of human hearing, equilibrium and other senses to produce complete disorientation and confusion. This is accomplished by: (1) interruption of the mechanical transduction process by which sound, position (relative to gravity) and other sensory input is converted to messages that are processed by the brain; and (2) interruption of the chemical engine which sustains the proper operation of nerve cells that respond to the mechanical transduction mechanisms. Interruption of either or both of these processes produces complete disorientation and confusion sufficient to temporarily and remotely render a human powerless to resist arrest or subjugation. Removal of the RF excitation of the targeted structure will leave the organs and surrounding tissues with no damage. The second order effects of severe motion sickness and the psychological effects of "helplessness" remains until the body chemistry returns to normal.

DESCRIPTION OF THE PREFERRED EMBODIMENTS

Human perception depends on the classical five senses of hearing, sight, smell, taste and touch. Along with these there are at least four other senses: equilibrioception (balance), proprioception (body awareness), thermoception (heat) and nociception (pain).

Vestibluar System

As commonly known to those skilled in the art, and as used herein, the term "vestibular" means: of, relating to, or affecting the perception of body position and movement and includes the sense of balance and perception stemming from communication between the inner ear, the eyes, and the central nervous system.

Figures 1, 2:
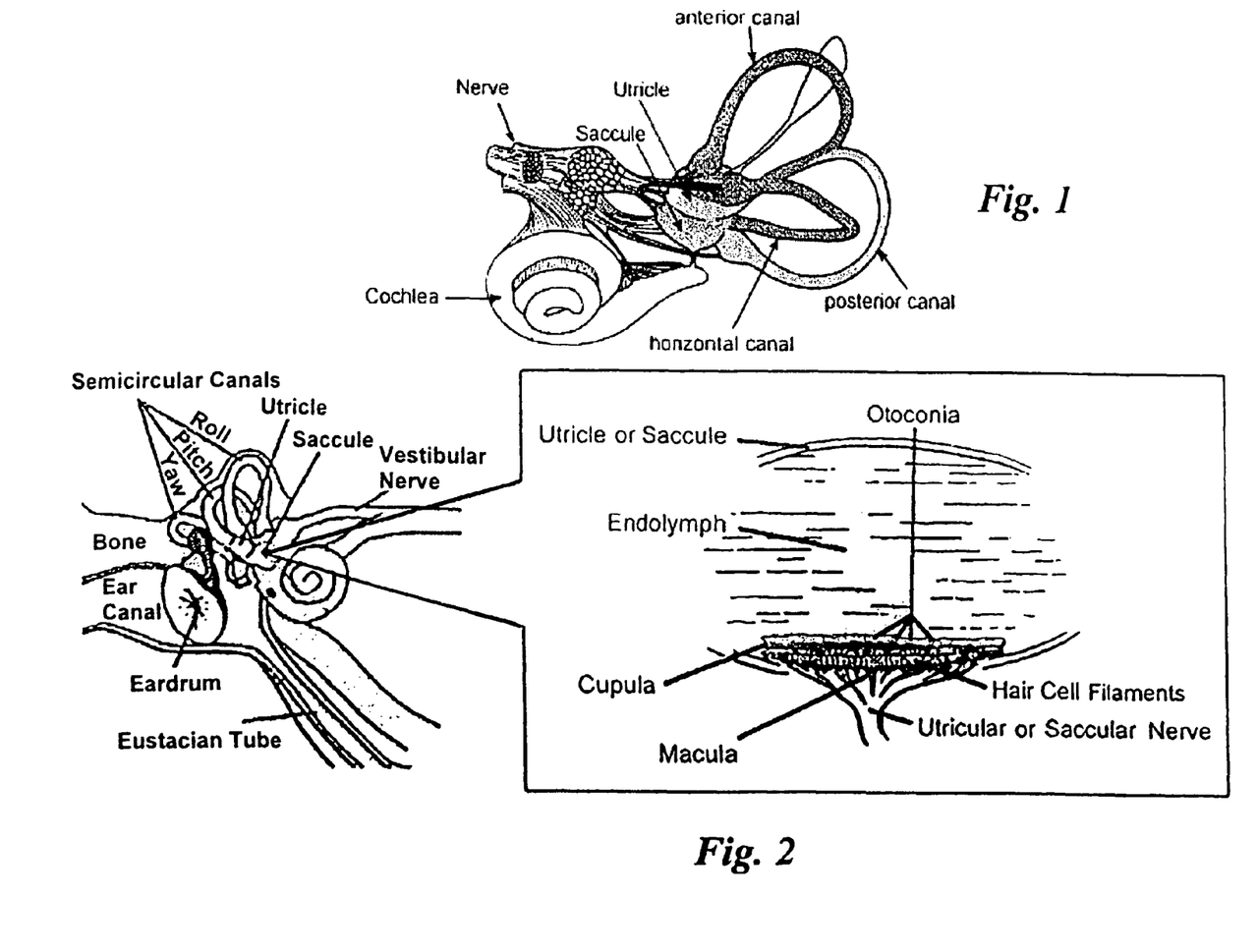
FIG. 1 is an illustration of the human membranous labyrinth with cochlea and vestibular system.
FIG. 2 is a schematic illustration of the otolith organs showing the details of the utricle, ococonia, endolymph, cupula, macula, hair cell filaments, and saccular nerve.

Referring to FIGS. 1 and 2, the auditory system is the sensory system for the sense of hearing. On its path from the outside world to the forebrain, sound information is preserved and modified in many ways. It changes media twice, first from air to fluid, then from fluid to "action potentials". Together with the cochlea and numerous liquid containing vesicles, the vestibular labyrinth forms the membranous labyrinth of the inner ear. It contains five separate specialized sensory receptors: three semicircular canals, and two otolith organs that complement each other in function. The semicircular canals (horizontal, anterior, and posterior) transduce rotational head movements (angular accelerations). The otolith organs (utricle and saccule) respond to translational head movements (linear accelerations) or to the orientation of the head relative to gravity. Each semicircular canal and otolith organ is spatially aligned to be most sensitive to movements in specific planes in three-dimensional space.

The vestibular system sends signals primarily to the neural structures that control our eye movements, and to the muscles that keep us upright. The projections to the former provide the anatomical basis of the vestibulo-ocular reflex, which is required for clear vision; and the projections to the muscles that control our posture are necessary to keep us upright.

Figure 3:
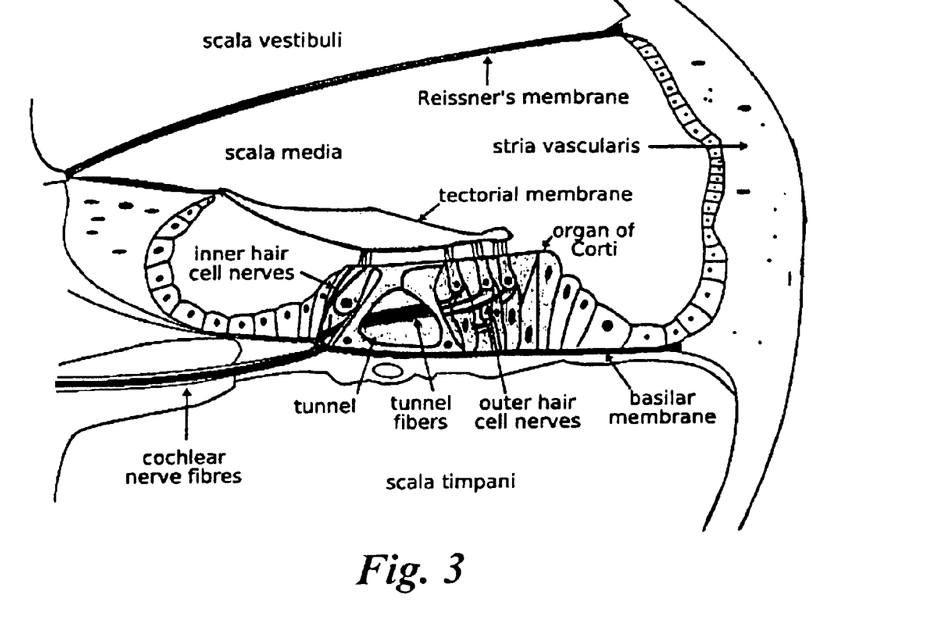
FIG. 3 is a schematic cross section through the cochlea.
Figure 4:
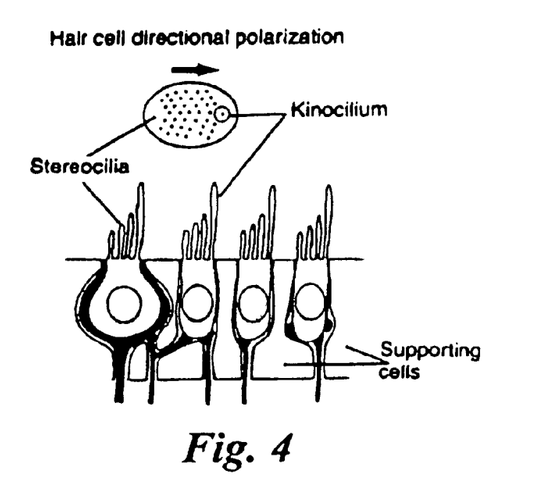
FIGS. 4, 5 and 6 are schematic illustrations of the ciliary hair bundle showing the hair cell directional polarization, ciliary transduction mechanism, and the deflection of the ciliary hair bundle toward and away from the kinocilium and the resultant change in conductivity.

As shown schematically in FIGS. 3, 4, 5 and 6, "hair cells" are the sensory receptor cells of the auditory system in all vertebrates. In mammals, the hair cells are located within the cochlea's organ of Corti (FIG. 3). They derive their name from the tufts of stereocilia that protrude from the apical surface of the cell, a structure known as the hair bundle. Each hair cell contains 60 to 100 hexagonally arranged stereocilia and a single longer kinocilium (FIG. 4). Mammalian hair cells come in two anatomically and functionally distinct types: the outer and inner hair cells (FIG. 3). Damage to these hair cells results in decreased hearing sensitivity, i.e. sensorineural hearing loss. Research of the past decades has shown that outer hair cells are motile and mechanically amplify low-level sound that enters the cochlea. The inner hair cells transform the sound vibrations in the fluids of the cochlea into electrical signals that are then relayed via the auditory nerve to the auditory brainstem and to the auditory cortex.

In the utricle and saccule hair cells, the otolithic membrane covers the stereocilia and its displacement excites the hair cells in unison. In the semicircular canals, the stereocilia are embedded in the gelatinous cupula that helps translate the motion of the endolymph that fills the canals into the unified motion of the hair cells residing in the cupula. In normal circumstances, the motion of the membranes will lag the head movements, creating a shearing distortion upon the underlying gel with cilia embedded in it.

As described above, the stereocilia are coupled to nerves. Excitation of these hairs activates nerve impulses that the brain interprets as sound or position relative to gravity. The nerves that connect the hairs and produce electrical impulses to the brain operate on the exchange of ionized calcium (Ca) and potassium (K) through semi-permeable cell membranes. Random and/or simultaneous excitation of all the hair/nerve combinations and the upset of the normal ionic chemistry produce sensations of intense wideband sound and complete disorientation which the brain has little or no hope of decoding.

Figure 5:
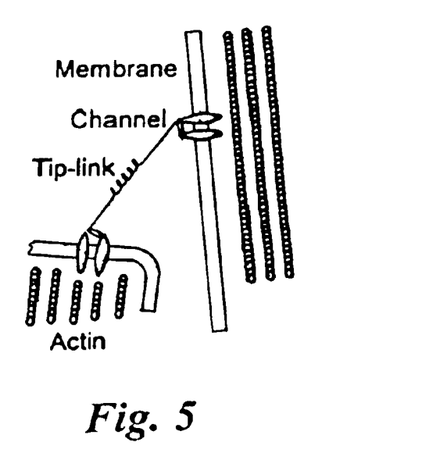
Figure 6:
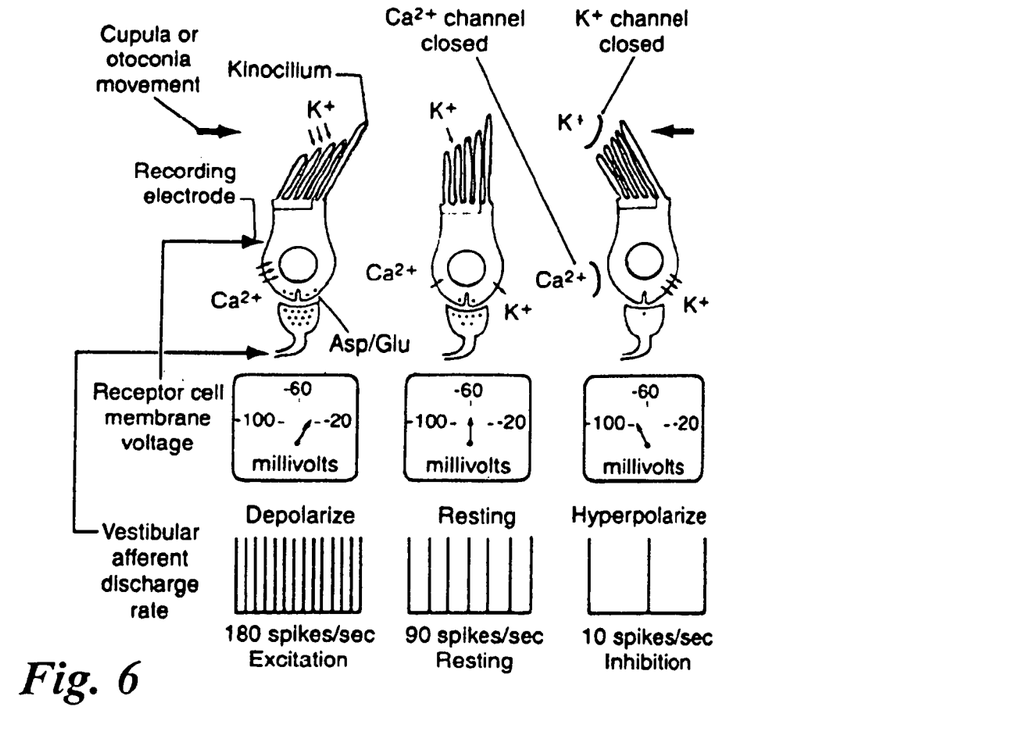

The hair cell transduction mechanism is depicted schematically in FIGS. 5 and 6. The deflection of the ciliary (hair) bundle towards or away from the kinocilium causes change in conductivity of the cilia. Variation of ciliary current in turn causes change in the membrane potential of the hair cell, which leads to variation in the firing rate of the neuron, associated with this hair cell. The axis along which the motion has the most effect is a polarization line.

To disrupt the vestibular function, the present electromagnetic wave (described in greater detail hereinafter) impinges on the vestibular organs. Interaction of the alternating magnetic field with the current in hair bundles perpendicular to wave propagation will create an alternating sideways force on the cilia containing the current, and therefore on the entire ciliary bundle. Swaying of the bundle will produce periodic hyperpolarization-depolarization pattern at the cellular membrane leading to the increased decreased-increased firing rate of the cells.

Figure 7:
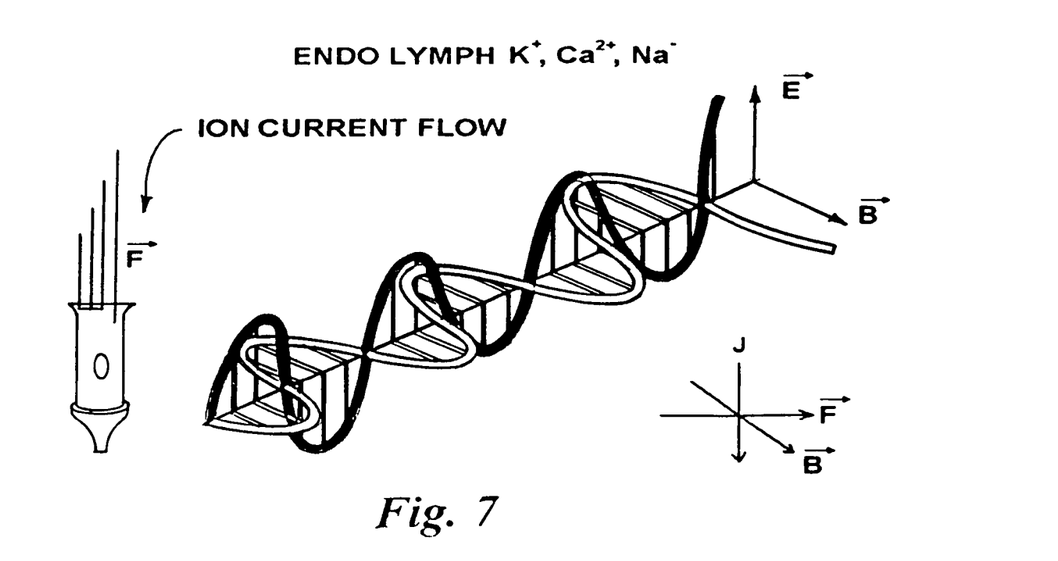
FIG. 7 is a schematic illustration of the electromagnetic wave.

The generic action and the representation of the electromagnetic wave (EMW) are illustrated schematically in FIGS. 6 and 7. The EMW has the electric field (heavier dark sinusoid) and the magnetic field (lighter sinusoid) alternating in phase in mutually perpendicular directions that are also perpendicular to the direction of the wave propagation. To begin, let us assume for an instant that magnetic field B is constant, and directed away from the reader, into the page. Positive potassium $K^+$ and calcium $Ca^{2+}$ ions flow down from outer end of the cilia towards cell body, and ciliary current J is also directed downwards according to the convention that current is directed along the motion of the positive charges. With the current directed down, and the magnetic field B directed into the page, the Lorentz force on the cilium F points to the right. Now, if the field changes the direction, the force will change the sign, too, pushing the cilium to the left. This will happen if the wave approaches the ciliary bundle from the right. The electric field now alternates in the vertical direction, whereas magnetic component sinusoidally oscillates in the direction perpendicular to the page, exerting horizontal (sideways) Lorentz force on the bundle.

Depending on the polarization and direction of the electromagnetic wave (EMW), different vestibular organs will be affected. The three cupulae, stretched across the ampullated end of each of the semicircular canals that act as transducers of angular accelerations, will be affected in their entirely. The sensory membranes in the saccule and utricle that transduce linear accelerations and static displacements have complex topology with several distinct excitation regions that are thought to be instrumental in distinguishing acceleration from head tilt by distinguishing the excitation patterns. Whatever is the excitation area, the stimulation will produce coherent input from the affected region, similar to what happens in normal circumstances. The effect of partial stimulation of either vestibular organ would be twofold: (1) as a result from the mismatch between the visual and vestibular sensory clues presented to the brain (vestibular system reports extraneous acceleration or motion that the eyes do not perceive); and (2) as a result of the unusual nature of the stimulus experienced by the vestibular system. The first action mechanism plays an up tight interconnection between visual and vestibular functions. Vestibular system inputs are used to steady the gaze during walking—a problem in early camcorders that lacked image stabilization filtration, when jumpy movies caused nausea in the viewers. This relation is amply demonstrated by the nausea associated with motion sickness when the brain cannot cope with mismatch between the visual clues of rest (no motion) and the vestibular clues of acceleration as happen on a ship or an airplane.

The second action mechanism borrows from the clinical observation of patients with Benign (Paroxysmal) Positional Vertigo (BPPV or BPV). Vertigo and syncope are the most common symptoms of BPPV, which are brought on by the contamination of the endolymph (liquid that fills semicircular canals responsible for detection of the angular accelerations) with otoconia crystals that have separated from otolith. Presence of the otoconia in the affected semicircular canal makes it gravity-sensitive, which results in the inappropriate input from the aforesaid semicircular canals. It is believed that it is the novelty of the stimulus that causes debilitating loss of balance that lasts from 30 to 60 seconds. Relaxation time is most probably a result of the viscous deceleration of the otoconia by surrounding endolymph liquid, rather than an indication of brain's capability for adaptation. Therefore, the system mimicking symptoms associated with BPPV would be a very satisfactory means of temporary incapacitation.

The present electromagnetic personnel interdiction control (EPIC) system and method seeks affect changes at the cellular level by applying a Lorentz force to the bundles with the aim to overdrive the hair bundle oscillating under a normal stimulus or to excite an oscillation of the hair bundle producing in both cases an extraneous, unanticipated signal that is not matched by any other senses. The external motion of the hair bundles causes a hair cell to generate corresponding ciliary current that results in the change of membrane potential. In their animal studies of the cilia motion under transepithelial (through the membrane) electrical stimulation, Hudspeth et al. found that at the frequencies above the hair bundle's natural frequency (35 and 8 Hz for two saccular hair cell bundles of the bullfrog studied), the bundles' oscillations were a superposition of the driving and natural frequencies. Bozovic D, Hudspeth, A. J., "Hair-bundle movements elicited by transepithelial electrical stimulation of hair cells in the sacculus of the bullfrog", Proc Natl Acad Sci USA. 2003 Feb. 4; 100(3):958-63.

These findings show the reciprocal nature of the mechano-chemical properties of the hair cells: the stimulation of the bundle causes changes on the membrane and vice versa. In the present system, we reciprocate these findings to conclude that if the ciliary bundle is driven at some frequency, there will be a response at the membrane, creating the desired neuronal activity that will be presented to the vestibular center in the brain.

Current knowledge of BPPV supports long-term effectiveness of the system. The fact that patients suffering from BPPV are usually instructed to relieve the symptoms by a series of controlled movements and absence of reports about the familiarization with the stimulus corroborate the argument that brain cannot learn and adapt to the stimulus within the timeframe of weapon usage and frequency of exposure. Moreover, from the chronic nature of the affliction, we deduce the potential to use the system repeatedly without losing its effectiveness.

The present system can also be modified to act at a more complex level. The vestibular system does not have the dynamic feedback of the cochlea, which lends so much complexity to the latter. There is no active processing and no continuous adaptation that makes our hearing so versatile. On the contrary, for secure functioning of the balance system, the vestibular inputs must always be the same, predictable and repeatable. The only "vestibular adaptation" is observed under continuous or frequent exposure to a stimulus. Researchers have described it as a "semi-premanent change of perception or perceptual-motor coordination that serves to reduce or eliminate a registered discrepancy between or within sensory modalities or the errors in behavior induced by this discrepancy". Return to original environment causes a renewed error, or aftereffect. Thus, repeated exposures to altered environment generally result in faster "adaptation". However, the learning applies only to that particular kind of stimulus. Therefore, the present system can act either by creating unusual sensations or by using more typical excitation in an on-off scheme.

The responses from all the hair cells in a cupula or a macula are coherent, and the brain has learned to recognize excitation patterns for various parts of the membrane, thus, varying the excitation patterns by only few hair cells may sufficient by itself to create a "panic" reaction in the brain, incapacitating the normal function.

The hair cell design is an amazing sensing mechanism with incredible dynamic range and equally incredible resolution throughout most of the dynamic range. The fundamental design of a hair cell has proven to be evolutionary stable. The hair cells of frogs, turtles and mammals are all very similar. Most easily observable differences between the hair cells of different species are the geometric factors (size, overall bundle height, step height, number of cilia, and packing of cilia) of the bundle. There are also differences in the adaptation process timescales as well as the magnitude of the adaptation observed in various species. This divergence is a result of evolutionary adjustment to the stimuli experienced by a given species.

Radio Frequency (RF) signal

Figure 8:
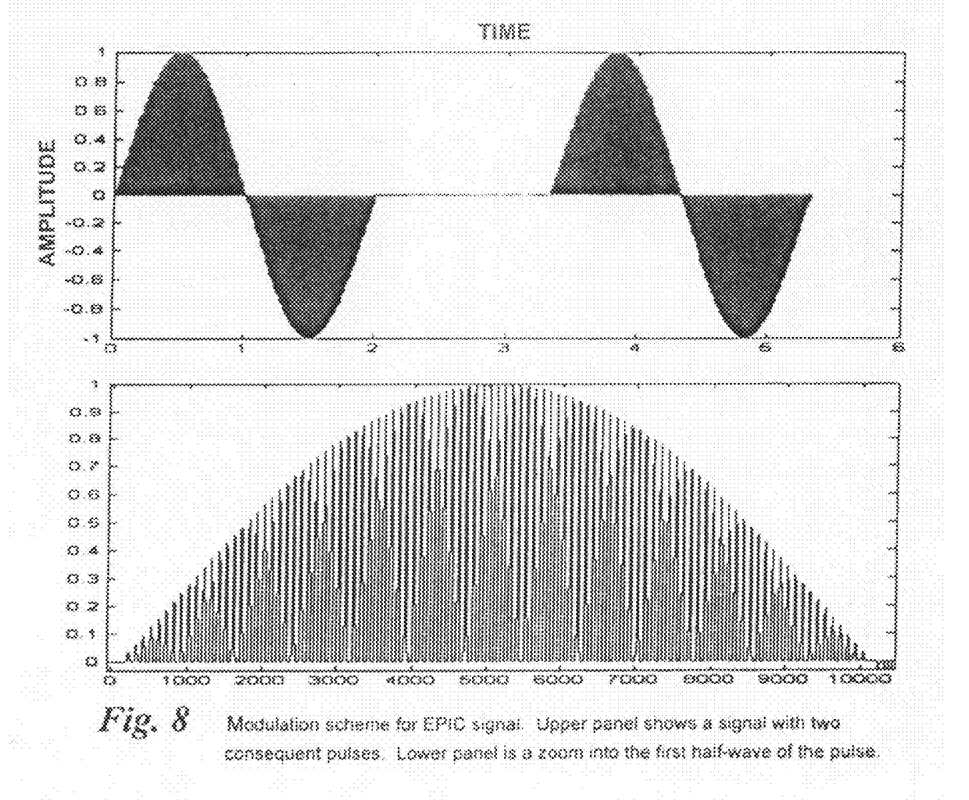
FIG. 8 is a graph illustrating an example of a signal modulation scheme.

FIG. 8 is a graph illustrating an example of a signal modulation scheme that was tested which fully utilizes the mechanical properties of the ciliary bundle. For the baseline power level estimate, we chose the average parameters for the hair cells measured and reported in published studies of various animal species. It is assumed that parameters of the mouse and human vestibular hair cells will not vary so much as to affect the power estimates by more than one order of magnitude. A higher radio frequency carrier is non-symmetrically modulated by a slower driving frequency for the hair bundles. This modulation scheme provides necessary permeability through most obstacles while maintaining good signal range. Displacement step and force step measurements show that the hair bundle acts as a low-pass filter integrating over high frequencies present in the input. Therefore, the hair bundle will act as an integrator for the higher frequency carrier, while fully responding to the modulation signal. Testing has shown that a carrier frequency in the 900 MHz Industrial, Scientific and Medical (ISM) band as defined by Federal Communications Commission, which is safely used by cellular phone operators, can reduce expected (non-existent) health concerns, and a driving frequency selected to be above most of the known natural frequencies of individual hair bundles (few to tens of Hz), and below the frequency of the utricular or saccular sensory system as a whole (few hundreds Hz), would avoid damage to the hair bundles by avoiding resonance where the bundle may be driven into too great an oscillation, and thereby maintain the non-lethal nature of the present system. Every other half-wave portion may be inverted to maximize the force on, and thus the displacement of, the hair bundle. This also lessens the signal power needed to achieve the same effect on the bundle.

Bundle Modeling and RF Power Level Current research indicates that the mechanical properties of the ciliary bundles yield similar order of magnitude figures for the dynamic properties of the hair bundles of outer hair cells of various species. The major source of differences can be ascribed to the evolutionary differences (i.e. frequency selectivity) in the hair cell morphology between the species. Moreover, most of the current research concentrates on the outer hair cells of the cochlea, as spontaneous activity of the latter is thought to give rise to spontaneous acoustic emissions from human ears. Two types of adaptation that alter dynamic properties of the hair bundles upon the stimulus have been observed; Fast and Slow. Slow adaptation happens within the time scales for neuronal processes, whereas fast adaptation occurs before the cellular membrane has changed polarization. Fast adaptation is believed to be meditated by the molecular motors involved in the mechano-transduction process. Most interestingly, it not only causes undesirable decrease in transduction current (at constant deflection), it also causes decrease in dynamic stiffness of the ciliary bundles. Although a decrease in the transduction current, occurring in the millisecond time scales (well below the intended stimulus) may hinder the influence of the present system; a decrease in dynamic stiffness after initial stimulation may contribute to the efficacy of present system.

Figure 9:
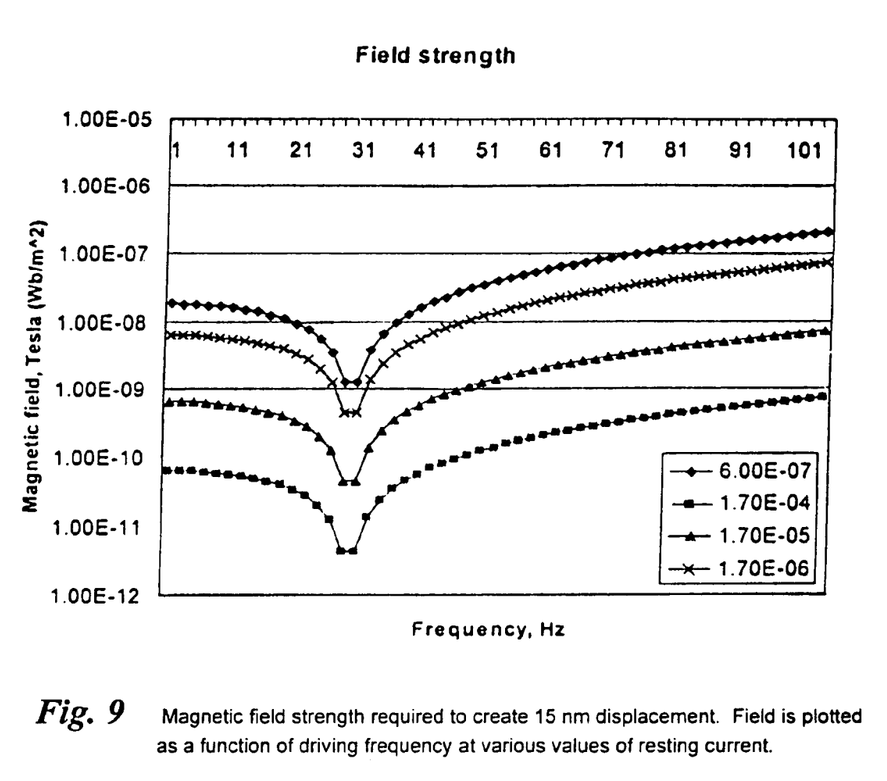
FIG. 9 is a graph showing the magnetic field strength required to create a 15 nm displacement of a ciliary hair bundle.

The following equations are a simplified model of the hair bundle that has been used for the estimates of the frequency and the field strength of the electromagnetic wave (EMW) required to achieve certain displacement of the hair bundle. In this model, the hair bundle is treated as one point mass at the center of mass of the bundle, and idealization of the bundle was manifest in the equal spacing between the bundles, equal density distribution among the cilia and along the length of each individual cilium. This model also assumes equal relative transducer efficiency at each cilium, and equal Lorentz force density among the cilia.

The damped oscillator, driven by a periodic force is described by equation of motion:

$$\ddot{x} + 2\eta\dot{x} + \omega_0^2 x = \frac{F_0}{M}\exp(i\gamma t),$$

where M is bundle mass, k-spring constant, $$\eta = \frac{c}{2M} - \text{damping factor}, \quad \omega_0^2 = \frac{k}{M} - \text{natural frequency},$$

c is viscous damping factor and $F_0$ is the amplitude of driving force. The dots above the variable denote order of a time derivative, so that $\ddot{x}$ is a second derivative of displacement, i.e. acceleration. Similarly, $\dot{x}$ is the velocity of the oscillator. After the transient natural damped responses have decayed, the driven system will oscillate at the driving frequency with the amplitude proportional to the natural frequency of the oscillator, the driving frequency, and the damping constant:

$$x_{max} = \frac{F_0}{M\sqrt{(\omega_0^2 - \gamma^2)^2 - 4\eta^2\gamma^2}}$$

The Lorentz force acting on a cilium is $\vec{F} = q(\vec{E} + \vec{V} \times \vec{B})$ The magnetic component of an electromagnetic wave propagating in z-direction can be described as following:

$$B_x(z,t) = B_0 \exp(-\{(z-v_g t)/l\}^2 + i(k_0 z - \omega_0 t + \theta))$$

The wave length of the EMW is so large with respect to the actual bundle size, that the field can be treated as same for entire bundle:

$$B_x(t)|_{z=fixed} = B_0 \cos(\omega_0 t + \theta').$$

The charge flowing through a small segment of a cilium is:

$$\delta Q = \frac{I}{v}\delta l.$$

Then the force on that fragment is $$\delta \vec{F} = \delta Q v B(\hat{v}\times\hat{B}) = I\delta l B(\hat{v}\times\hat{B}).$$

Therefore, the force on the entire cilium $$\vec{F} \approx IlB(\hat{v}\times\hat{B}) = IlB_0(z)\cos(\omega_0 t+\theta')(\hat{v}\times\hat{B})$$

Generalizing the result to an entire bundle, we obtain magnitude of Lorentz force acting on the bundle:

$$|F|=IBL,$$

where I is total ciliary current, L is total length of the cilia in the bundle, B is the magnetic field strength. Substituting the force magnitude into the expression of the displacement, and resolving it with respect to the magnetic field amplitude, we arrive at the field strength needed to create an oscillation of amplitude $x_{max}$:

$$B = \frac{x_{max} M \sqrt{(\omega_0^2-\gamma^2)^2 - 4\eta^2\gamma^2}}{IL}$$

FIG. 9 is a graph showing the magnetic field strength required to create a 15 nm displacement of a ciliary hair bundle. Field is plotted as a function of driving frequency at various values of resting ciliary current. The calculation for signal strengths was carried out using the mechanical and electrical characteristics of turtle cochlear hair cells. Most researchers agree that the mechanoelectrical properties of the vestibular cells are close in different species subject to similar vestibular inputs. Therefore, it is realistic to expect not more than one order of magnitude variation between mammals (humans, mice) and amphibians (frog and turtles). A resonant frequency 30 Hz was selected for power estimate calculations. The desired displacement was selected to be about 15 nm in order to affect a 3 mV hyper/de-polarization on the cell membrane, which is 60% of total hyper/de-polarization of ±5 mV with respect to −65 mV of normal polarization at the outer hair cell membrane. Resting transduction current was extrapolated through the conductivity measurements. With resulting numbers differing widely, and taking into account that the hair cells to be affected may already have some significant deflection, power levels were calculated for several possible values of resting ciliary current. It should be emphasize that this is a very conservative estimate, wherein worst-case values were used when no exact values were available. The results are presented in Table 1 below. The power density values of the driving frequency chosen for initial testing are set in boldface.

TABLE 1

Power of the wave at several frequencies required to sway idealized bundle by 15 nm.
Power density, W/m²

| Current, A/ Frequency, Hz | 1.70E−04 | 1.70E−05 | 1.70E−06 | 6.00E−07 |
| --- | --- | --- | --- | --- |
| 15 | 6.04E−07 | 6.04E−05 | 6.04E−03 | 4.85E−02 |
| 51 | 3.83E−06 | 3.83E−04 | 3.83E−02 | 3.08E−01 |
| 101 | 1.15E−04 | 1.15E−02 | 1.15E+00 | 9.20E+00 |
| 200 | 2.03E−03 | 2.03E−01 | 2.03E+01 | 1.63E+02 |
| 300 | 1.05E−02 | 1.05E+00 | 1.05E+02 | 8.44E+02 |
| 400 | 3.35E−02 | 3.35E+00 | 3.35E+02 | 2.69E+03 |
| 500 | 8.22E−02 | 8.22E+00 | 8.22E+02 | 6.60E+03 |

Figure 10:
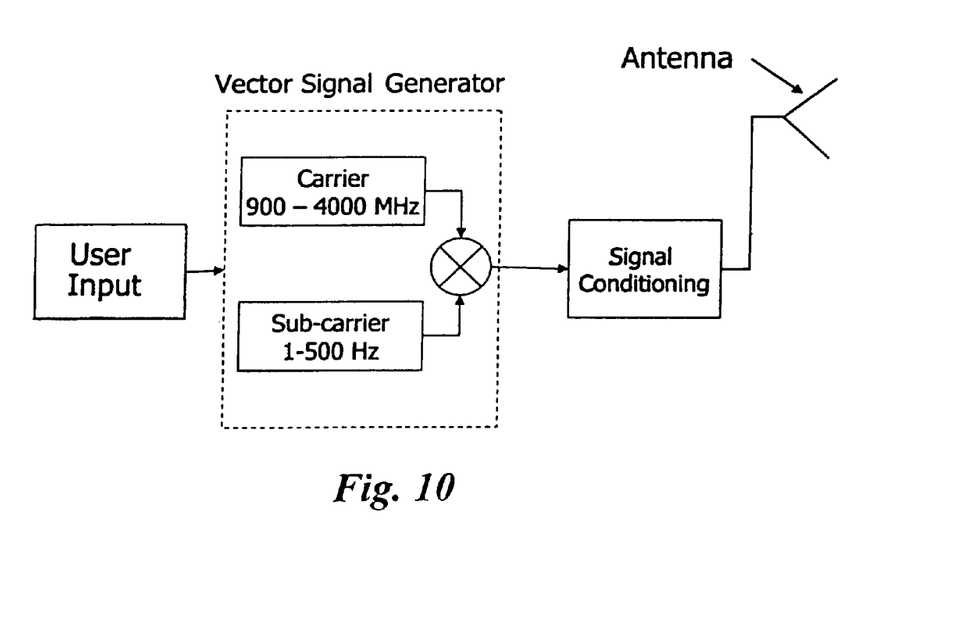
FIG. 10 is a block diagram illustrating a typical electromagnetic personnel interdiction control (EPIC) system.

FIG. 10 is a block diagram illustrating a typical electromagnetic personnel interdiction control (EPIC) system. The frequency and the field strength of the electromagnetic wave (EMW) and RF signal required to achieve a desired displacement or stimulation of the hair bundle or cell is calculated in accordance with the equations set forth above, along with the parameters of carrier frequency, modulation frequency, shape of the modulation waveform, and transmit power. Once the desired waveforms have been identified, a commercially available vector signal generator with one or more amplifiers is used to provide the output power and one or more antennas is used to direct the generated signal to the desired target.

Figure 11:
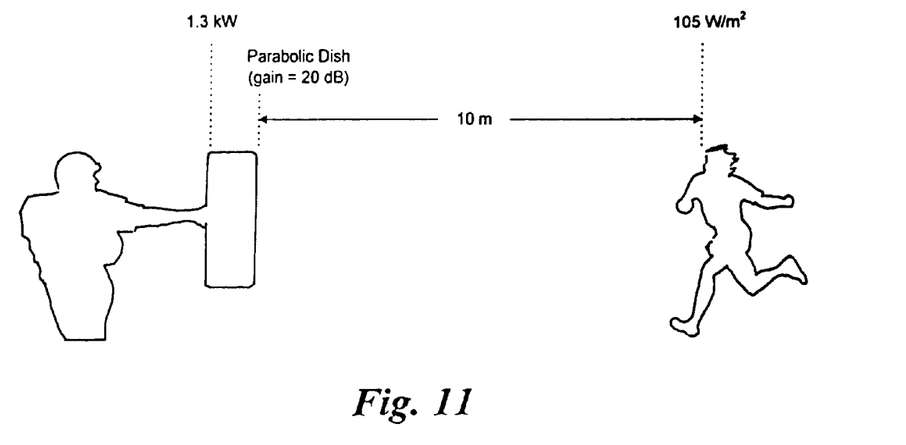
FIG. 11 is a schematic illustration showing a person aiming the antenna of the electromagnetic personnel interdiction control (EPIC) system at an attacker.

FIG. 11 is a schematic illustration showing on the left-hand side a person aiming the antenna (parabolic dish) of the electromagnetic personnel interdiction control (EPIC) system at an attacker on the right-hand side. In this example, for a 15 nm displacement (4% of full dynamic range), 1.7μA ciliary current was required to produce 105 W/m² at the bundle using a carrier of 915 MHz, a driving frequency of 300 Hz, and 1.3 KW transmit power and an antenna with 20 dB gain, produced 5 nW on the attacker's hair bundle at a distance of 10 m.

Relatively long relaxation time of the BPPV symptoms and measured learning times of "vestibular adaptation" indicate that there may be no need to emit another RF pulse until the effects of the initial impulse wear out. Thus, the present system can be pulsed to promote portability and minimize individual exposure, and thereby allow longer system operation time and reduced device size.

Cochlea and Retina Tissues

In the examples above, the electromagnetic (EM) radiation with unique modulation imposed a Loretz force on the stereocilia in the vestibular system causing them to move and impact the cell pulse propagation to the brain that the brain could not decode. It should be understood that these same forces may be placed on similar tissues in the cochlea and retina tissues to cause disruption of the ion flow that regulates the nerve pulse output to the brain in ways that the brain cannot decode. The electromagnetic field and subsequent surface charges on those tissues would change the impedance of the conduction capabilities, disturb the ion flow, and subsequently impact the pulse output of the cells to the brain. The interruption of normal ion flow would cause pulse patterns to the brain that it cannot decode.

Visual perception is the ability to detect light and interpret (see) it as the perception known as sight. Vision has a specific sensory system, the visual system. The retina contains photoreceptor cells (rods and cones) which receive the light; the resulting neural signals then undergo complex processing by other neurons of the retina, and are transformed into "action potentials" in retinal ganglion cells whose axons form the optic nerve. The retina not only detects light, it also plays a significant part in visual perception.

Rods and cones are both photosensitive, but respond differently to different frequencies of light. They both contain different pigmented photoreceptor proteins. Rod cells contain the protein rhodopsin and cone cells contain different proteins for each color-range. The process through which these proteins go is quite similar—upon being subjected to electromagnetic radiation of a particular wavelength and intensity (ie. a color visible light) the protein breaks down into two constituent products. Rhodopsin, of rods, breaks down into opsin and retinal; iodopsin of cones breaks down into photopsin and retinal. The opsin in both opens ion channels on the cell membrane which leads to the generation of an action potential (an impulse which will eventually get to the visual cortex in the brain). This is the reason why cones and rods enable organisms to see in dark and light conditions—each of the photoreceptor proteins requires a different light intensity to break down into the constituent products. Furthermore, color is distinguishable when breaking down the iodopsin of cone cells because there are three forms of this protein. One form is broken down by the particular EM wavelength that is red light, another green light, and lastly blue light. In simple terms, this allows human beings to see red, green and blue light. If all three forms of cones are stimulated equally, then white is seen. If none are stimulated, black is seen.

Static Charge on Cell Membrane

The normal operation of the cells of the ear, vestibular system, and the eye can also be disrupted by positively or negatively charged pulsed EM (Electromagnetic) energy imposed upon the cells to increase or decrease the magnitude of the static charge of the "electron rich" site that surrounds the ion trapdoor or cation channel in the hair conductor or cell membrane. This would adversely affect the cells' attraction to calcium (Ca) and/or potassium (K) ions and thereby impact the rate of ion flow and the ultimate pulse rate of the cells. Uncorrelated data would then be fed to the brain and the brain would have no basis for decoding, thereby creating disorientation.

Altering the normal electromagnetic field and subsequent surfaces charges on the tissues of the ear, vestibular system and the eye can change the impedance of their conduction capabilities, disturb the ion flow, and subsequently impact the pulse output of the cells to the brain. This interruption of normal ion flow would cause pulse patterns to the brain that it cannot decode, thereby creating disorientation.

Other cells, Muscular Function and Nerve Pathways

The normal electrochemical balance of substantially all of the cells of the human body relative to the rest of the body fluids can be disrupted by altering the relative charge level to cause the cells to activate the protein doors or channels in the cell wall that allow unidirectional passage of negative charge sodium (Na) ions and the opposite passage of positively charged calcium (Ca) ions, thereby causing hyperactive chemical exchanges that can negatively impact the system and disrupt normal smooth and striated muscular functions.

The application of pulses of voltage directly to nerve paths can also feed uncorrelated sensory input data to the brain that would ultimately produce some level of disorientation.

Other Applications

Controlled stimulus of the vestibular system in humans could also produce beneficial results. Although the current effort is aimed at temporary disruption of vestibular functions for purposes of controlled incapacitation, it may be possible to create "selective" stimulation that can produce physiological sensations that replicate emergency and other high-stress situations. Such situations currently require training to identify, understand, and constructively react to threats of various types.

One specific example is pilot training for aircraft operation under instrument conditions. Pilots are required to be able to control and maneuver aircraft vehicles without reference to the horizon. While in IMC (Instrument Meteorological Conditions) the pilot's vestibular system is a liability. This is because the inherent stability of the aircraft creates a false gravity to which the vestibular system reacts. This effect causes the pilot (based on internal vestibular data sent to the brain) to believe that the aircraft is flying straight and level when; in fact, the aircraft could be in some unusual attitude. For example, when a loop is flown correctly, at the time the pilot is inverted at the top of the loop, his vestibular systems is telling him that he is right side up and flying straight and level. Thus, considerable training is required to condition pilots to ignore their vestibular sensory inputs and focus on flight instruments to achieve spatial orientation.

Instrument training is expensive and recurring training is required to maintain skill levels that will assure the safety of the aircraft and passengers. The airlines spend hundreds of millions of dollars per year on initial and recurrent flight training. The military has an added challenge. Combat pilots are subjected to extreme G forces as aircraft maneuver to obtain superior positioning over an opponent. These skills and the mental concentration and physiological resistance to G forces must be constantly conditioned by complex flight and combat simulations as well as actual flight simulation of combat scenarios.

Selectively applied, EPIC stimulus may be able to reproduce "sensations" in pilots-in-training that accurately simulate actual "upset" and map G force conditions encountered in flight without need of moving platforms under the flight simulators. Such a capability would reduce the costs of flight training while enhancing the reality of the emergency and/or combat conditions for which the training is offered.

The EPIC system could be used for treatment of BPPV patients who do not respond to conventional treatment by positional exercises. These patients are usually subjected to a surgical procedure to block the afflicted semicircular canal, which somewhat undermines their balance. Since the system emulates the effects of the BPV, its effect may be tuned to each particular form of BPPV to counteract the symptoms. Treatment like this will eliminate the need for surgical correction.

While this invention has been described fully and completely with special emphasis upon preferred embodiments, it should be understood that within the scope of the appended claims the invention may be practiced otherwise than as specifically described herein.

The invention claimed is:

1. A non-lethal method for immobilizing a human subject by utilizing electromagnetic energy to disrupt the subject's sense of balance and perception of body position and movement, comprising the steps of:

providing means for generating and transmitting a beam of radio frequency electromagnetic energy having a selected frequency and modulation correlated to a physical and a chemical structure of a human sensory cell to disrupt proper operation of either of a mechanical transduction process or a chemical process by which sensory input is converted by the sensory cell to messages that are processed by a human brain; and directing said beam of radio frequency electromagnetic energy from a remote location toward the human subject to be immobilized to impose a Lorentz force on selected sensory cells of the subject sufficient to disrupt proper operation of the cell's mechanical transduction process or chemical process and alter the sensory input converted to messages processed by the subject's brain to adversely affect the perception of body position and movement so as to produce disorientation, confusion, and incapacitation sufficient to immobilize and render the subject powerless to resist arrest or subjugation.

2. The method according to claim 1, wherein
said step of directing said beam of radio frequency electromagnetic energy from a remote location toward the human subject to be immobilized comprises imposing a Lorentz force on sensory receptor hair cells of vestibular organs of the subject's inner ear that are connected by auditory nerves operating on exchange of ionized calcium and potassium through semi-permeable cell membranes to produce electrical impulses through the auditory brainstem to the auditory cortex of the brain which interprets the nerve impulses as sound or position relative to gravity; and
said Lorentz force causing random excitation or movement of said hair cells so as to disrupt the exchange of ionized calcium and potassium and produce sensations of intense wideband sound and confusion between the subject's visual perception and the vestibular sensations transmitted to the subject's brain that affect the subject's perception of the subject's body position relative to gravity resulting in disorientation sufficient to immobilize and render the subject powerless to resist arrest or subjugation.

3. The method according to claim 1, wherein
said step of directing said beam of radio frequency electromagnetic energy from a remote location toward the human subject to be immobilized comprises imposing a Lorentz force on cells of the subject's cochlea and retina tissues such that electromagnetic field and subsequent surface charges on the cochlea and retina tissues changes the impedance of their conduction capabilities to disrupt ion flow that regulates nerve pulse output to the subject's brain and produce confusion between the subject's visual perception and the vestibular sensations transmitted to the subject's brain that affect the subject's perception of the subject's body position relative to gravity resulting in disorientation sufficient to immobilize and render the subject powerless to resist arrest or subjugation.

4. The method according to claim 1, wherein
said step of directing said beam of radio frequency electromagnetic energy from a remote location toward the human subject to be immobilized comprises imposing positively or negatively charged pulsed electromagnetic energy on sensory receptor stereocilia hair cells of vestibular organs of the subject's inner ear to increase or decrease the magnitude of a static charge of an electron-rich site surrounding a cation channel in a hair conductor or cell membrane to alter its attraction to calcium and or potassium ions thereby altering the rate of ion flow and producing a resultant uncorrelated pulse rate of the cells of the subject's ears, vestibular system, and eyes that is transmitted to the subject's brain and adversely affect the subject's perception of the subject's body position relative to gravity to produce disorientation sufficient to immobilize and render the subject powerless to resist arrest or subjugation.

5. The method according to claim 1, wherein
said step of directing said beam of radio frequency electromagnetic energy from a remote location toward the human subject to be immobilized comprises imposing pulses of said electromagnetic energy to cells of the subject's body so as to disrupt a proper electrochemical balance within the cells relative to other fluids of the subject's body whereby the cells exchange waste and nutrients and maintain an electrochemical balance with the rest of the body; and
said pulses of said electromagnetic energy imposed on the cells excite cell areas into hyperactive chemical exchanges between negatively charge sodium ions and positively charged calcium ions to cause an adverse effect on the electrochemical balance of the subject's body and disruption of smooth and striated muscular functions sufficient to immobilize and render the subject powerless to resist arrest or subjugation.

6. The method according to claim 1, wherein
said step of providing means for generating and transmitting said beam of radio frequency electromagnetic energy comprises calculating a frequency and a field strength of the electromagnetic wave and radio frequency signal required to achieve a displacement or stimulation of selected sensory cells of the subject effective to disrupt proper operation of the cells mechanical transduction process or chemical process;
calculating a parameter of carrier wave frequency, modulation frequency, shape of a modulation waveform, and transmission power;
providing a vector signal generator and at least one amplifier coupled with said vector signal generator to generate a power output in accordance with the recited calculations, and at least one antenna coupled with said power output; and
said step of directing said beam of radio frequency electromagnetic energy from a remote location comprises aiming said antenna toward the human subject to be immobilized.

* * * * *